US010575802B2

(12) United States Patent
Bouhnik et al.

(10) Patent No.: US 10,575,802 B2
(45) Date of Patent: Mar. 3, 2020

(54) SYSTEMS AND METHODS FOR CONTROLLING MOTION OF DETECTORS HAVING MOVING DETECTOR HEADS

(71) Applicant: General Electric Company, Schenectady, NY (US)

(72) Inventors: Jean-Paul Bouhnik, Zichon Yaacov (IL); Yaron Hefetz, Kibbutz Alonim (IL)

(73) Assignee: General Electric Company, Schenectady, NY (US)

(*) Notice: Subject to any disclaimer, the term of this patent is extended or adjusted under 35 U.S.C. 154(b) by 973 days.

(21) Appl. No.: 14/040,108

(22) Filed: Sep. 27, 2013

(65) Prior Publication Data

US 2015/0094574 A1 Apr. 2, 2015

(51) Int. Cl.
*A61B 6/00* (2006.01)
*A61B 6/03* (2006.01)

(52) U.S. Cl.
CPC ............ *A61B 6/4266* (2013.01); *A61B 6/032* (2013.01); *A61B 6/037* (2013.01); *A61B 6/4258* (2013.01); *A61B 6/4275* (2013.01); *A61B 6/4291* (2013.01); *A61B 6/4417* (2013.01); *A61B 6/4429* (2013.01); *A61B 6/5235* (2013.01); *A61B 6/54* (2013.01)

(58) Field of Classification Search
CPC .... G01T 1/1615; G01T 1/1648; G01T 1/2985
See application file for complete search history.

(56) References Cited

U.S. PATENT DOCUMENTS

| 3,543,384 | A | * | 12/1970 | Hansen | A61B 1/04 250/363.1 |
| 5,506,408 | A | * | 4/1996 | Vickers | G01T 1/1642 250/366 |
| 6,140,650 | A | | 10/2000 | Berlad | |
| 6,239,438 | B1 | | 5/2001 | Schubert | |
| 6,388,244 | B1 | * | 5/2002 | Gagnon | G01T 1/1615 250/208.1 |

(Continued)

FOREIGN PATENT DOCUMENTS

WO  2008135994 A2  11/2008

OTHER PUBLICATIONS

A PCT Search Report and Written Opinion issued in connection with related Application No. PCT/IL2014/050848 dated Feb. 5, 2015.

(Continued)

*Primary Examiner* — Joseph M Santos Rodriguez
(74) *Attorney, Agent, or Firm* — Dean D. Small; The Small Patent Law Group, LLC

(57) ABSTRACT

Systems and methods for controlling motion of detectors having moving detector heads are provided. One system includes a gantry and a plurality of detector units mounted to the gantry, wherein the plurality of detector units are individually movable including translational movement and rotational movement. The system further includes a controller configured to control movement of the plurality of detector units to acquire Single Photon Emission Computed Tomography (SPECT) data, wherein the movement includes both the translational movement and the rotational movement coordinated to position the plurality of detector units adjacent to a subject.

15 Claims, 17 Drawing Sheets

(56) References Cited

U.S. PATENT DOCUMENTS

| | | | |
|---|---|---|---|
| 6,748,044 B2 | 6/2004 | Sabol et al. | |
| 6,943,355 B2 | 9/2005 | Shwartz et al. | |
| 7,026,623 B2 | 4/2006 | Oaknin et al. | |
| 7,381,959 B2 | 6/2008 | Manjeshwar et al. | |
| 7,671,331 B2 | 3/2010 | Hefetz | |
| 8,280,124 B2 | 10/2012 | Dichterman et al. | |
| 2002/0191828 A1 | 12/2002 | Colbeth et al. | |
| 2005/0145797 A1 | 7/2005 | Oaknin et al. | |
| 2006/0108532 A1 | 5/2006 | Ohana et al. | |
| 2007/0018108 A1 | 1/2007 | Kitamura | |
| 2008/0029704 A1* | 2/2008 | Hefetz | A61B 6/037 250/363.01 |
| 2008/0304619 A1* | 12/2008 | Blevis | G21K 1/025 378/16 |
| 2010/0310037 A1* | 12/2010 | Wang | A61B 6/032 378/6 |
| 2012/0108948 A1 | 5/2012 | Jansen et al. | |
| 2012/0205542 A1 | 8/2012 | Goedicke et al. | |
| 2013/0034200 A1* | 2/2013 | Hsieh | A61B 6/03 378/7 |
| 2013/0168567 A1 | 7/2013 | Wartski et al. | |

OTHER PUBLICATIONS

Meikle et al., "Accelerated Em reconstruction in total-body PET: potential for improving tumour delectability," 1994, 1 Physics in Medicine and Biology, vol. 39, pp. 1689-1704.

Riddell et al., "Noise reduction in oncology FOG PET images by iterative reconstruction: a quantitative assessment," 2001, the Journal of Nuclear Medicine, vol. 42, No. 9, pp. 1316-1323.

Shepp et al., "Maximum likelihood reconstruction for emission tomography," 1982, IEEE Transaction on Medical Imaging, vol. MI-1, No. 2, pp. 113-122.

Park et al., "Performance of a high-sensitivity dedicated cardiac SPECT scanner for striatal uptake quantification in the brain based on analysis of projection data," Med. Phys. 40 (4), Apr. 2013.

\* cited by examiner

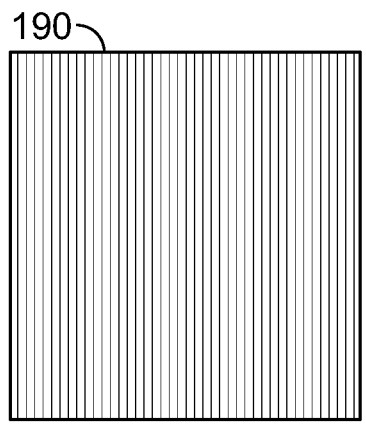
(a)
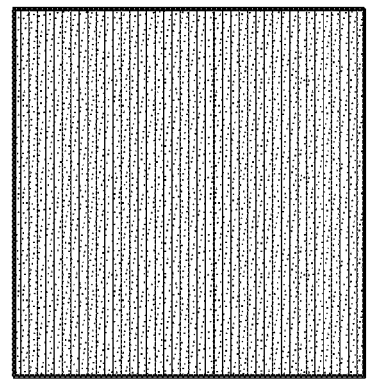
(b)
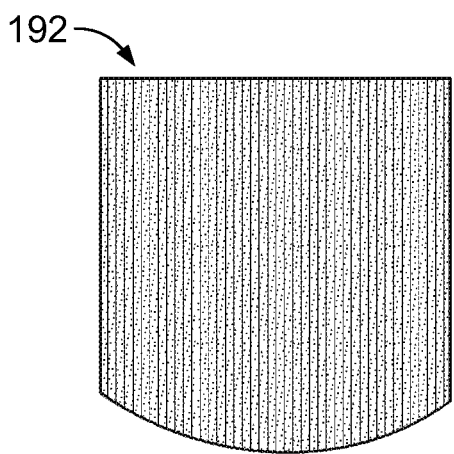
(c)
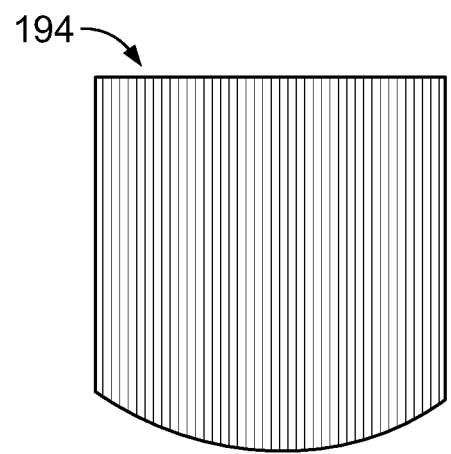
(d)
FIG. 7

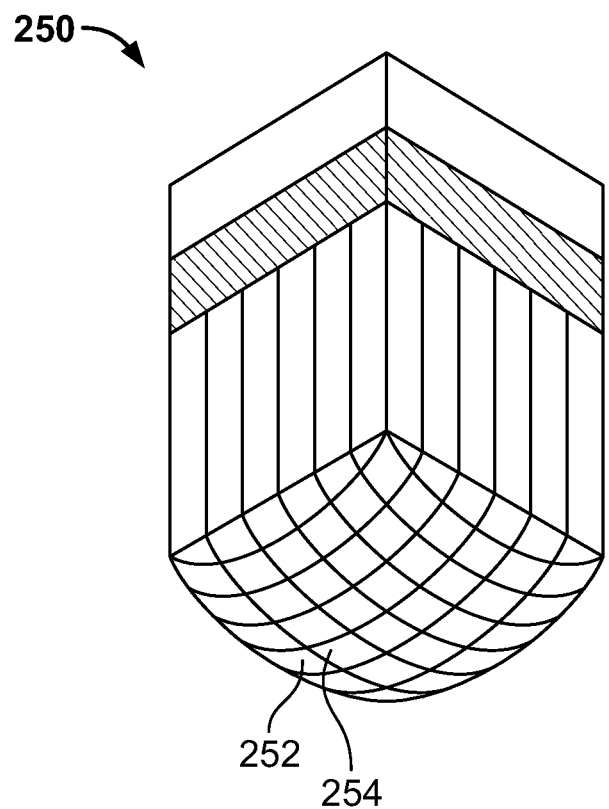
250, 252, 254
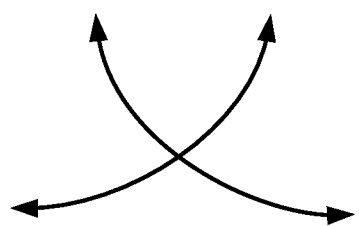
FIG. 12

SYSTEMS AND METHODS FOR CONTROLLING MOTION OF DETECTORS HAVING MOVING DETECTOR HEADS

BACKGROUND OF THE INVENTION

The subject matter disclosed herein relates generally to apparatus and methods for diagnostic medical imaging, such as Nuclear Medicine (NM) imaging.

In NM imaging, systems with multiple detectors or detector heads may be used to image a subject, such as to scan a region of interest. For example, the detectors may be positioned adjacent the subject to acquire NM data, which is used to generate a three-dimensional (3D) image of the subject.

Single Photon Emission Computed Tomography (SPECT) systems may have moving detector heads, such as gamma detectors positioned to focus on a region of interest. For example, a number of gamma cameras may be moved (e.g., rotated) to different angular positions for acquiring image data. The acquired image data is then used to generate the 3D images.

Resolution of gamma detectors is a convolution of the detector resolution (mainly pixel size) and the collimator resolution. Collimator resolution degrades with the distance of the collimator from the patient. In conventional SPECT camera systems with multiple swinging detector heads, the detectors swing about a fixed pivot (usually inside a protective case). As a result of the configuration of these systems, including the detectors and collimators, the gamma cameras often have to be placed at an additional distance from the patient. This increase in distance results in a degrading of resolution.

Thus, known systems have degradation in imaging resolution as a result of the limits to which the gamma cameras can move in proximity to the patient because of the configuration of the detector head or collimator used, and/or the types of control of movement of the gamma cameras.

BRIEF DESCRIPTION OF THE INVENTION

In one embodiment, an imaging system is provided that includes a gantry and a plurality of detector units mounted to the gantry, wherein the plurality of detector units are individually movable including translational movement and rotational movement. The imaging system further includes a controller configured to control movement of the plurality of detector units to acquire Single Photon Emission Computed Tomography (SPECT) data, wherein the movement includes both the translational movement and the rotational movement coordinated to position the plurality of detector units adjacent to a subject.

In another embodiment, an imaging system is provided that includes a plurality of pivoting detector units and at least one collimator coupled to at least one of the pivoting detector units. The collimator includes collimator bores of different lengths to form a non-planar face.

In another embodiment, a method for collimating a Nuclear Medicine (NM) detector is provided. The method includes providing a collimator having a plurality of collimator bores extending through a body portion, where at least some of the collimator bores have different lengths to form a curved face along one side of the body portion. The method also includes configuring the collimator for coupling to at least one detector module.

BRIEF DESCRIPTION OF THE DRAWINGS

FIG. 7 is a diagram illustrating the manufacture of a collimator in accordance with an embodiment.

FIG. 12 is a diagram illustrating a collimator arrangement in accordance with another embodiment.

DETAILED DESCRIPTION OF THE INVENTION

Figure 1:
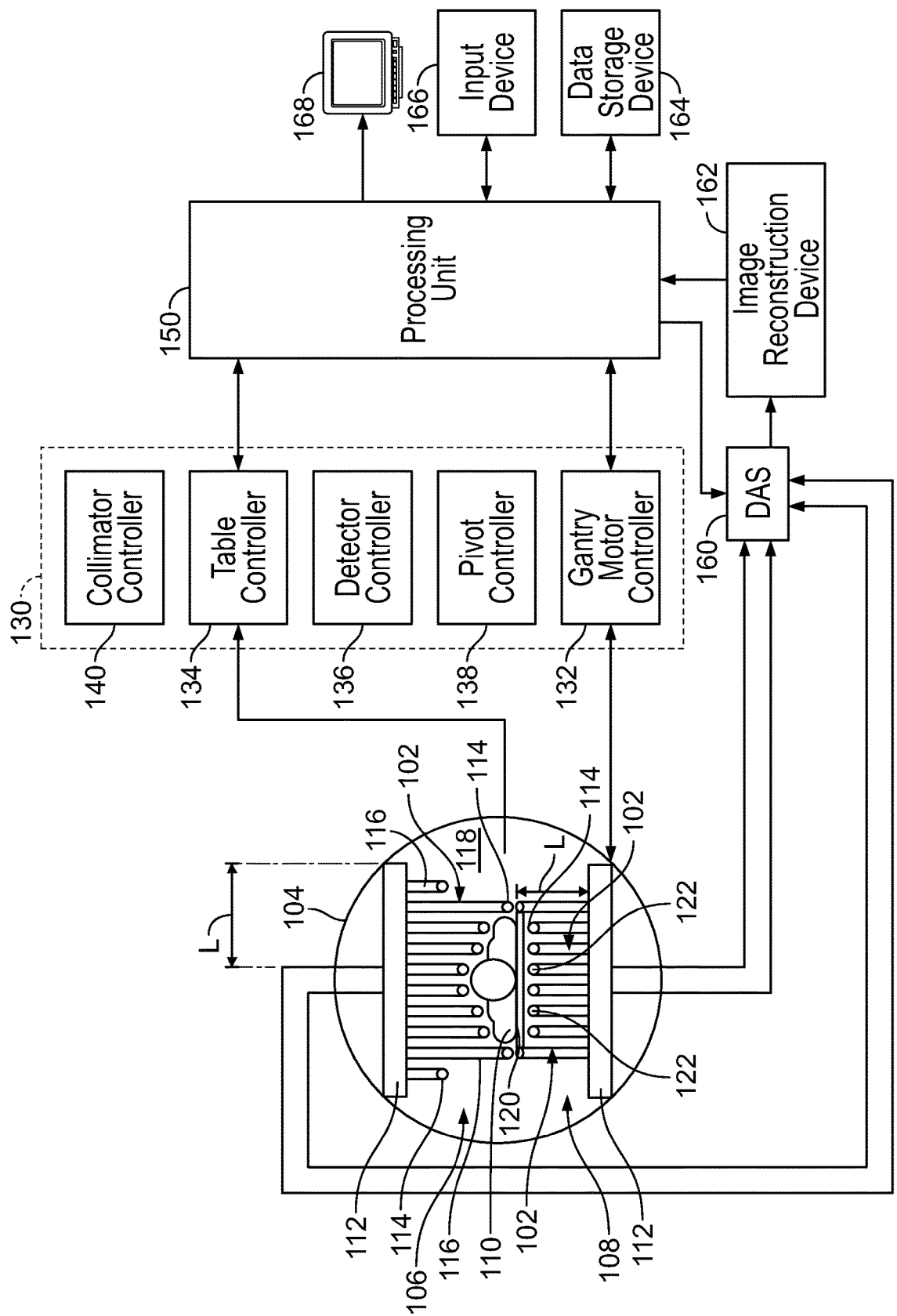
FIG. 1 is a schematic block diagram of a Nuclear Medicine (NM) imaging system in accordance with an embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for controlling the movement of a plurality of imaging detectors to position the imaging detectors to acquire image data. For example, in various embodiments, an imaging system having one or more Nuclear Medicine (NM) cameras having an array of heads that are individually and independently movable is provided. In some embodiments, one or more of the heads are capable of a plurality of types of movement, such as translation, rotation, pivoting, and/or swiveling. The NM cameras in various embodiments are configured to acquire Single Photon Emission Computed Tomography (SPECT) data, such as when moving the detector heads. For example, various embodiments provide combination movements or complex motion of the detectors, such as a combination of up/down movement with swinging motion. In some embodiments, the motion may include, for example, side-to-side motion.

Additionally, imaging detectors or camera heads are coupled with collimators in various embodiments. In some embodiments, collimators are provided that have uneven bores, in particular, bores having different lengths. For example, instead of having collimators that are "box like" shaped with all bores having the same length, different length bores (e.g., uneven lengths) may be provided. In some embodiments, the varying collimator bore length increases resolution at the central or middle section of the detector and reduced or eliminates a gap between adjacent detectors.

FIG. 1 is a schematic illustration of a NM imaging system 100 having a plurality of imaging detectors mounted on a gantry (which may be mounted, for example, in rows, in an iris shape, or other configurations). In particular, a plurality of imaging detectors 102 are mounted to a gantry 104. In the illustrated embodiment, the imaging detectors 102 are configured as two separate detector arrays 106 and 108 coupled to the gantry 104 above and below a subject 110 (e.g., a patient), as viewed in FIG. 1. The detector arrays 106 and 108 may be coupled directly to the gantry 104, or may be coupled via support members 112 to the gantry 104 to allow movement of the entire arrays 106 and/or 108 relative to the gantry 104 (e.g., translating movement in the left or right direction as viewed in FIG. 1). Additionally, each of the imaging detectors 102 includes a detector unit 114, at least some of which are mounted to a movable detector carrier 116 (e.g., a support arm or actuator that may be driven by a motor to cause movement thereof) that extends from the gantry 104. In some embodiments, the detector carriers 116 allow movement of the detector units 114 towards and away from the subject 110, such as linearly. Thus, in the illustrated embodiment the detector arrays 106 and 108 are mounted in parallel above and below the subject 110 and allow linear movement of the detector units 114 in one direction (indicated by the arrow L), illustrated as perpendicular to the support member 112 (that are coupled generally horizontally on the gantry 104). However, other configurations and orientations are possible as described herein. It should be noted that the movable detector carrier 116 may be any type of support that allows movement of the detector units 114 relative to the support member 112 and/or gantry 104, which in various embodiments allows the detector units 114 to move linearly towards and away from the support member 112.

Each of the imaging detectors 102 in various embodiments are smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 102 may include one or more detector units 114 coupled to a respective detector carrier 116 and having dimensions of 4 cm to 20 cm and may be formed of Cadmium Zinc Telluride (CZT) tiles or modules. For example, each of the detector units 114 may be 8×8 cm in size and be composed of a plurality of CZT pixelated modules (not shown). For example, each module may be 4×4 cm in size and have 16×16=256 pixels. In some embodiments, each detector unit 114 includes a plurality of modules, such as an array of 1×7 modules. However, different configurations and array sizes are contemplated including, for example, detector units 114 having multiple rows of modules.

It should be understood that the imaging detectors 102 may be different sizes and/or shapes with respect to each other, such as square, rectangular, circular or other shape. An actual field of view (FOV) of each of the imaging detectors 102 may be directly proportional to the size and shape of the respective imaging detector.

The gantry 110 may be formed with an aperture 118 (e.g., opening or bore) therethrough as illustrated. A patient table 120, such as a patient bed, is configured with a support mechanism (not shown) to support and carry the subject 110 in one or more of a plurality of viewing positions within the aperture 118 and relative to the imaging detectors 102. Alternatively, the gantry 104 may comprise a plurality of gantry segments (not shown), each of which may independently move a support member 112 or one or more of the imaging detectors 102.

The gantry 104 may also be configured in other shapes, such as a "C", "H" and "L", for example, and may be rotatable about the subject 110. For example, the gantry 104 may be formed as a closed ring or circle, or as an open arc or arch which allows the subject 110 to be easily accessed while imaging and facilitates loading and unloading of the subject 110, as well as reducing claustrophobia in some subjects 110.

Additional imaging detectors (not shown) may be positioned to form rows of detector arrays or an arc or ring around the subject 110. By positioning multiple imaging detectors 102 at multiple positions with respect to the subject 110, such as along an imaging axis (e.g., head to toe direction of the subject 110) image data specific for a larger FOV may be acquired more quickly.

Each of the imaging detectors 102 has a radiation detection face, which is directed towards the subject 110 or a region of interest within the subject. The radiation detection faces are each covered by or have coupled thereto a collimator 122. The actual FOV for each of the imaging detectors 102 may be increased, decreased, or relatively unchanged by the type of collimator 122. As described in more detail herein, in some embodiments, the collimator 122 includes at least some collimator bores having different axial lengths.

In one embodiment, the collimator 122 is a multi-bore collimator, such as a parallel hole collimator. However, other types of collimators, such as converging or diverging collimators may optionally or alternatively be used. Other examples for the collimator 122 include pinhole, parallel-beam converging, diverging fan-beam, converging or diverging cone-beam, multi-bore converging, multi-bore converging fan-beam, multi-bore converging cone-beam, multi-bore diverging, or other types of collimator.

Optionally, multi-bore collimators may be constructed to be registered with pixels of the detector units 114, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or inbetween two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 130 may control the movement and positioning of the patient table 110, imaging detectors 102 (which may be configured as one or more arms), gantry 104 and/or the collimators 122 (that move with the imaging detectors 102 in various embodiments, being coupled thereto). A range of motion before or during an acquisition, or between different image acquisitions, is set to maintain the actual FOV of each of the imaging detectors 102 directed, for example, towards or "aimed at" a particular area or region of the subject 110 or along the entire subject 110. The motion may be a combined or complex motion in multiple directions simultaneously, concurrently, or sequentially as described in more detail herein.

The controller unit 130 may have a gantry motor controller 132, table controller 134, detector controller 136, pivot controller 138, and collimator controller 140. The controllers 130, 132, 134, 136, 138, 140 may be automatically commanded by a processing unit 150, manually controlled by an operator, or a combination thereof. The gantry motor controller 132 may move the imaging detectors 102 with respect to the subject 110, for example, individually, in segments or subsets, or simultaneously in a fixed relationship to one another. For example, in some embodiments, the gantry controller 132 may cause the imaging detectors 102 and/or support members 112 to move relative to or rotate about the subject 110, which may include motion of less than or up to 180 degrees (or more).

The table controller 134 may move the patient table 120 to position the subject 110 relative to the imaging detectors 102. The patient table 120 may be moved in up-down directions, in-out directions, and right-left directions, for example. The detector controller 136 may control movement of each of the imaging detectors 102 to move together as a group or individually as described in more detail herein. The detector controller 136 also may control movement of the imaging detectors 102 in some embodiments to move closer to and farther from a surface of the subject 110, such as by controlling translating movement of the detector carriers 116 linearly towards or away from the subject 110 (e.g., sliding or telescoping movement). Optionally, the detector controller 136 may control movement of the detector carriers 116 to allow movement of the detector array 106 or 108. For example, the detector controller 136 may control lateral movement of the detector carriers 116 illustrated by the L arrow (and shown as left and right as viewed in FIG. 1). In various embodiments, the detector controller 136 may control the detector carriers 116 or the support members 112 to move in different lateral directions.

The pivot controller 138 may control pivoting or rotating movement of the detector units 114 at ends of the detector carriers 116 and/or pivoting or rotating movement of the detector carrier 116. For example, one or more of the detector units 114 or detector carriers 116 may be rotated about at least one axis to view the subject 110 from a plurality of angular orientations to acquire, for example, 3D image data in a 3D SPECT or 3D imaging mode of operation. The collimator controller 140 may adjust a position of an adjustable collimator, such as a collimator with adjustable strips (or vanes) or adjustable pinhole(s).

It should be noted that motion of one or more imaging detectors 102 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 136 and pivot controller 138 may be combined to provide the different movements described herein.

Prior to acquiring an image of the subject 110 or a portion of the subject 110, the imaging detectors 110, gantry 104, patient table 120 and/or collimators 122 may be adjusted as discussed in more detail herein, such as to first or initial imaging positions, as well as subsequent imaging positions. The imaging detectors 102 may each be positioned to image a portion of the subject 110. Alternatively, one or more of the imaging detectors 102 may not be used to acquire data, such as the imaging detectors 102 at ends of the detector arrays 106 and 108, which as illustrated in FIG. 1 are in a retracted position away from the subject 110. Positioning may be accomplished manually by the operator and/or automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 114 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 102, gantry 104, patient table 120, and/or collimators 122 are positioned, one or more images, such as three-dimensional (3D) SPECT images are acquired using one or more of the imaging detectors 102, which may include using a combined motion that reduces or minimizes spacing between detector units 114. The image data acquired by each imaging detector 102 may be combined and reconstructed into a composite image or 3D images in various embodiments.

In one embodiment, at least one of detector arrays 106 and/or 108, gantry 104, patient table 120, and/or collimators 122 are moved after being initially positioned, which includes individual movement of one or more of the detector units 114 (e.g., combined lateral and pivoting movement). For example, at least one of detector arrays 106 and/or 108 may be moved laterally while pivoted. Thus, in various embodiments, a plurality of small sized detectors, such as the detector units 114 may be used for 3D imaging, such as when moving or sweeping the detector units 114 in combination with other movements.

In various embodiments, a data acquisition system (DAS) 160 receives electrical signal data produced by the imaging detectors 102 and converts this data into digital signals for subsequent processing. However, in various embodiments, digital signals are generated by the imaging detectors 102. An image reconstruction device 162 (which may be a processing device or computer) and a data storage device 164 may be provided in addition to the processing unit 150. It should be noted that one or more functions related to one or more of data acquisition, motion control, data processing and image reconstruction may be accomplished through hardware, software and/or by shared processing resources, which may be located within or near the imaging system 100, or may be located remotely. Additionally, a user input device 166 may be provided to receive user inputs (e.g., control commands), as well as a display 168 for displaying images.

Figure 2:
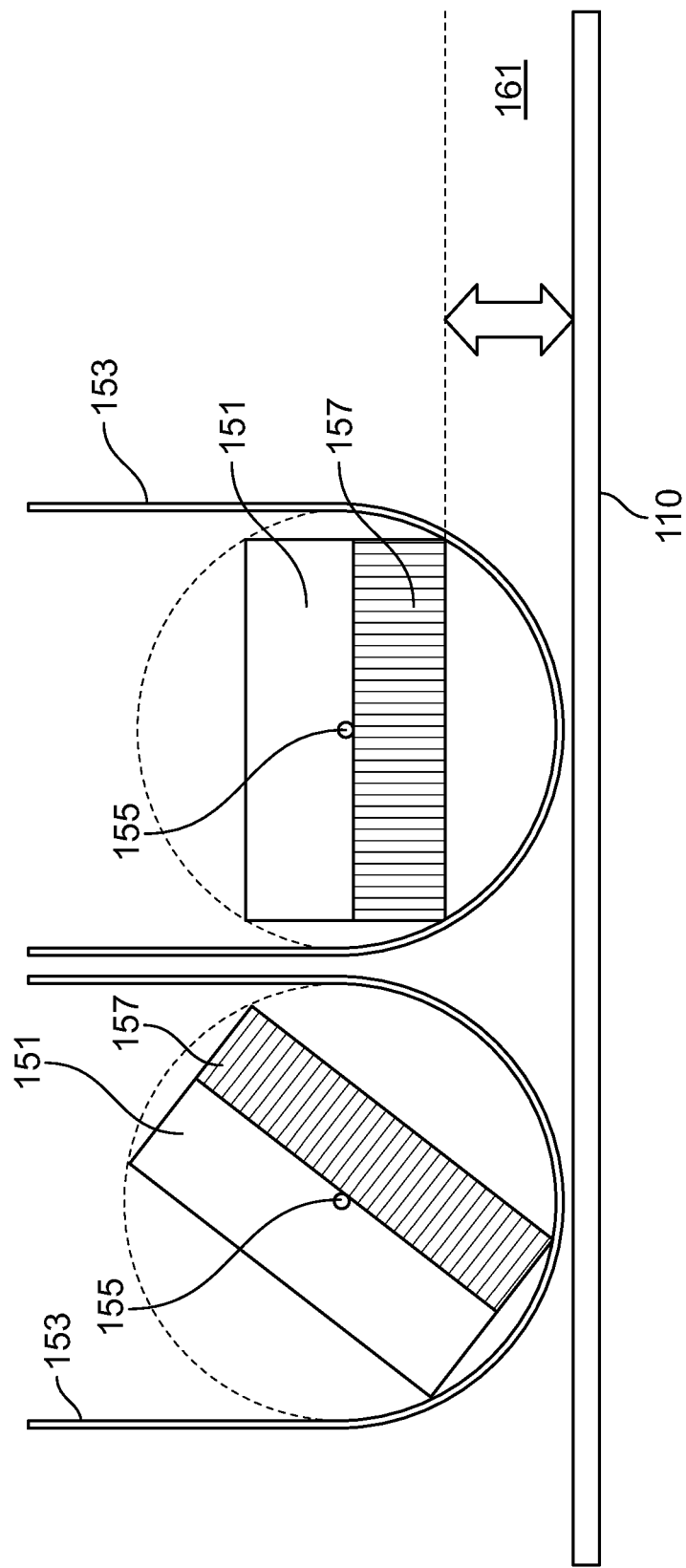
FIG. 2 is a diagram illustrating detectors having movement about one axis.

FIG. 2 schematically demonstrates a detector 151 within a housing 153 having only a single rotating or pivoting point. In this configuration, when the detector 151 (e.g., a CZT detector) is equipped with a flat collimator 157 (e.g., collimator having a planar face) is to rotate about a fixed pivot point 155, in order to avoid collision with a subject 110 (illustrated as a substantially flat patient), an unavoidable gap 161 is created between the face of the collimator 157 and the subject 110.

Figure 3:
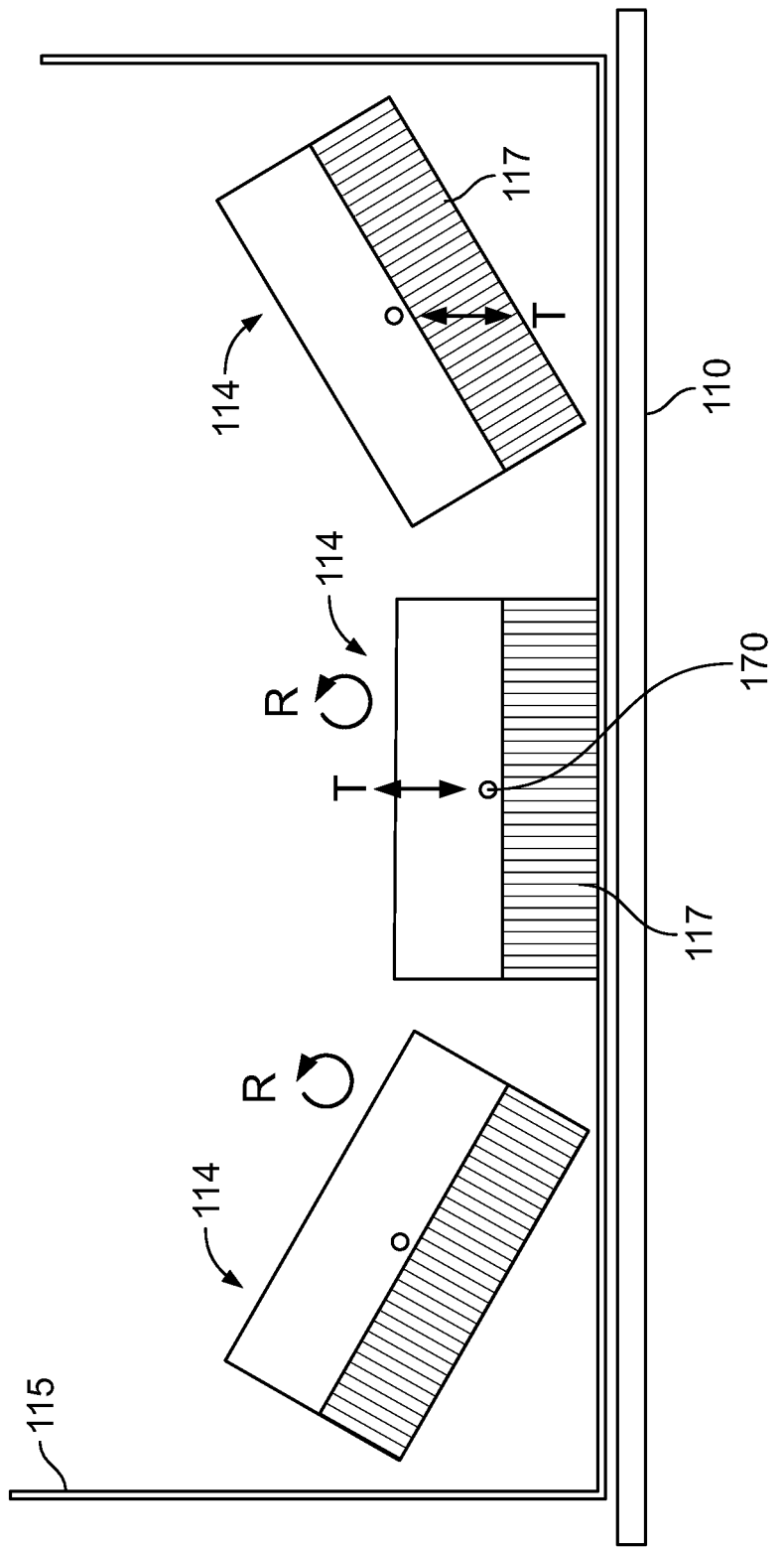
FIG. 3 is a diagram illustrating uncovered detectors in accordance with various embodiments.

In operation, and as shown, for example, in FIG. 3, a combined motion of the detector units 114 is used to position the detector units 114 or move the detector units 114 before, during, and/or after imaging. FIG. 3 schematically depicts a plurality of detector units 114, all within one patient-protecting cover 115. The coordinated rotational (or pivoting) and up/down motion seen in FIG. 3 are performed by each of the detector units 114 to reduce or minimize the distance from the face of the collimator 117 and the subject 110. The optional cover 115 may be removed, for example, when the detector units 114 are placed below the patient table 120

More particularly, as shown in FIG. 3, one or more of the detector units 114 may be positioned or repositioned using a combination of movements that are performed is some embodiments concurrently. It should be noted that the movements of different detector units 114 likewise may be performed simultaneously, concurrently, or sequentially. As illustrated in FIG. 3, one type of combined movement includes rotational movement (illustrated by the R arrow, which may be or include pivoting movement in some embodiments) and linear or translation movement (illustrated by the T arrow). It should be noted that while the translation movement is illustrated as up and down in FIG. 2, translation movement in other transverse or perpendicular directions may be provided, such as left and right.

Additionally, the rotating movement may be provided about different rotating axes or points, such as about a rod or at a pivot point. In FIG. 2, the rotation is about an axis 170, which may be a rotation or pivot point. For example, depending on the orientation of the axis 170, the detector units 114 may rotate in different directions.

Figure 4:
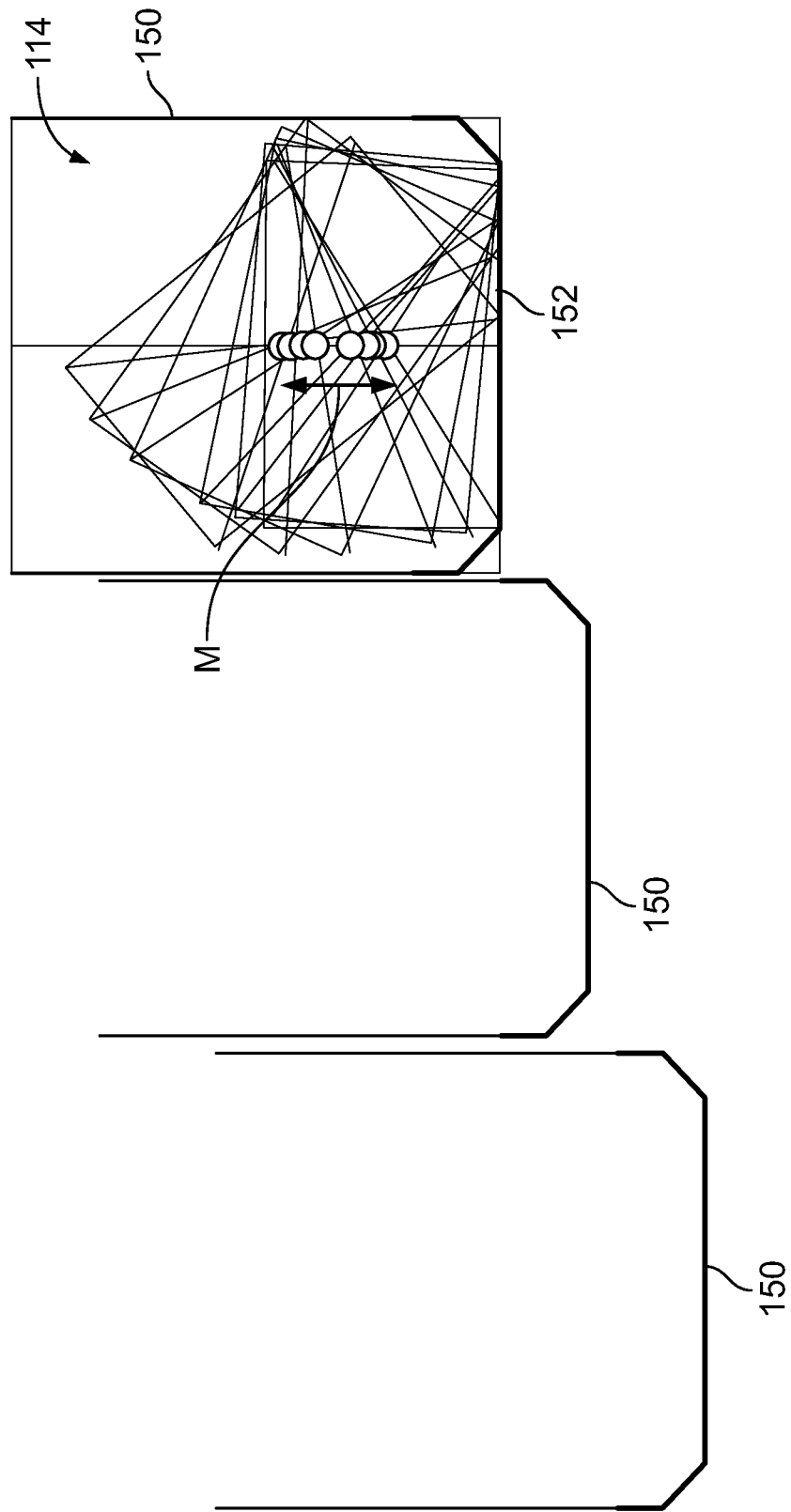
FIG. 4 is a diagram illustrating detector movement in accordance with various embodiments.

It should be noted that depending on the state of movement of the detector units 114 and the position thereof, a distance D exists between the detector units 114 and the front face 174 of the housing (not shown) of the detector units 114. For example, as illustrated in FIG. 4, a plurality of detector units 114 each having a respective housing 150 may be provided. As can be seen, a range of motion (illustrated by the M arrow) within the housing may be provided (up and down as seen in FIG. 4) in addition to rotational movement (and may be defined or set based on the object to be scanned). The rightmost detector unit 114 in FIG. 4 shows a movement pattern in accordance with one embodiment that allows the housings 150 to be positioned adjacent each other with reduced or minimal distance therebetween. As can be seen, by translating and rotating the detector units 114, the angle of the detector units 114 may be changed to focus the detector units 114 at different views, while maintaining a small footprint for the housing 150. In some embodiments, no housings 150 are provided.

It should be noted that the various movements of the detector units 114 may be provided using any suitable drive and control means, such as using one or more motors. Additionally or optionally, a proximity sensor 152 or other patient safety device may be used to detect contact or impending contact with a patient. The proximity sensor 152 may be provided in some embodiments as known in the art.

Figure 5:
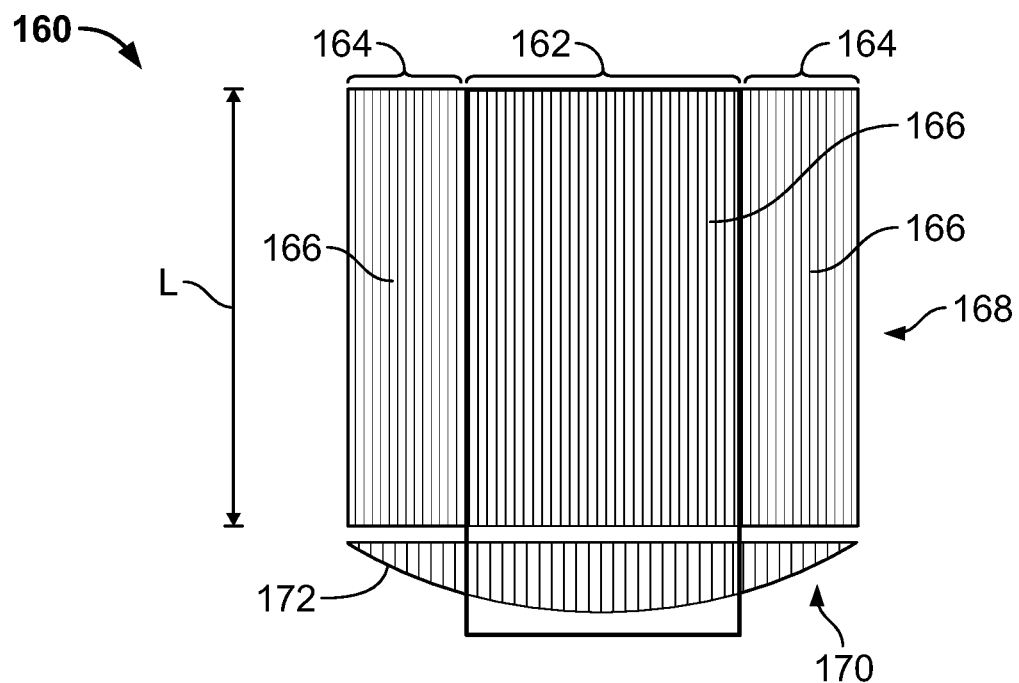
FIG. 5 is a diagram illustrating a collimator in accordance with an embodiment having a higher resolution area.

In various embodiments, a collimator 160 arrangement may be provided having variable length bores, for example, as illustrated in FIG. 5. In this embodiment, collimator bores 166 in a middle section 162 of the collimator 160 have a greater length (and different lengths) than the collimator bores 166 in side sections 164 of the collimator 160. Accordingly, as a result of the longer bore lengths in the middle section 162, a higher resolution imaging portion or area is defined when compared to the shorter lengths of collimator bores 166 in the side sections 164 (as distance from the object being scanned is related to resolution). In the illustrated embodiment, a top portion 168 and a bottom portion 170 of the collimator are shown as separate merely for ease of explanation and illustration and in various embodiments the collimator bores 166 from top to bottom as seen in FIG. 5 are single channels or pieces.

As can be seen in the illustrated embodiment, the length of the collimator bores 166 decreases from a middle of the middle section 162, through the middle section 162 and to ends of the end sections 164. Thus, in this embodiment, a smoothly curved or arcuate face 172 is formed. It should be noted that the curvature of the face 172 may be varied by changing the amount that the lengths of the collimator bores 166 (such as adjacent collimator bores 166) are different. It should also be noted that some of the collimator bores 166 may have the same length, such as adjacent collimator bores 166 or collimator bores 166 on opposite sides (from left to right) of the collimator 160. Additionally, it should be noted that the face in various embodiments is not limited to be smoothly curved, but may take different configurations, such as other different non-planar configurations (e.g., concave, convex, polygonal, among others).

In some embodiments, the amount of curvature may be varied at only certain portions along the face 172 to change the slope of the curve or different amount of curvature may be provided such as to provide an asymmetric face 172. Additionally, other variations and modifications are contemplated. For example, the length of the collimator bores 166 may be varied differently such as in a stepwise manner such that a smooth face 172 is not provided.

Figure 6:
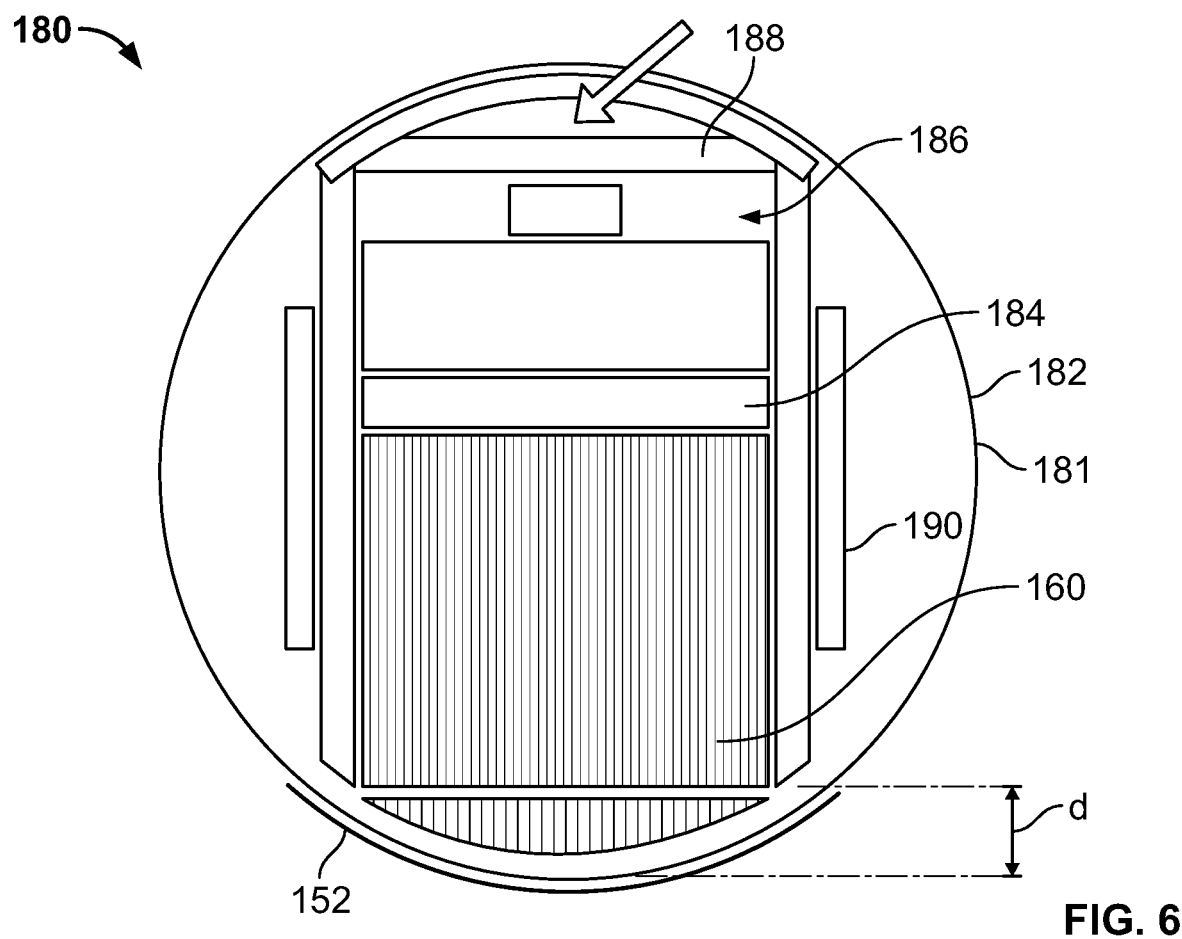
FIG. 6 is a diagram illustrating a collimator arrangement in accordance with an embodiment.

The collimator 170 may be provided as part of the imaging unit 114 to define a variable sensitivity and resolution detector module 180 as shown in FIG. 6. Thus, with the collimator 170, variable sensitivity and resolution may be provided that allows for focused scanning with only a portion of the module 180, for example, performing focused scanning using only image data acquired within the middle section 162. In one embodiment, focused scanning with a partial module may be performed for high resolution brain imaging.

It should be noted that although the housing of the module 180 is illustrated as circular (e.g., circular cross-section) within the circular cross-section region 181 in various embodiments, the housing may have different shapes as desired or needed. Additionally, the location of the components in the module 180 may be varied and different configurations or sizes also may be provided. In the illustrated embodiment, a detector material 184 (such as CZT) is positioned adjacent and behind the collimator 160 as viewed in FIG. 5. In one embodiment, the detector material 184 may have a pixelated structure that is registered with the collimator bores 166 (e.g., one pixel per collimator bore 166). Electronics 186 are coupled to the detector material 184, such as known in the art to read out signals to be processed. Additionally, shielding 188 is provided around the collimator 160, detector material 184, and electronics 186. A holder 190 or other support (e.g., bracket) is provided within the housing, which may take a configuration to maintain the position of the components therein or allow movement as described in more detail herein.

Modifications and variations are contemplated. For example, air cooling may be provided through an aperture (not shown), such as in the shielding 188 on the top of the module 180 as viewed in FIG. 6. It should be noted that the resolution at the central portion of the collimator 172 is further improved as the face of the collimator 172 at a central portion is closer to the subject 110 (as well as having longer bores). For example, the distance seen in FIG. 2 (showing a conventional detector arrangement) is avoided at least for some portion of the face of the collimator and some pivot positions. This increase in resolution may contribute to better image quality.

The collimator 160 may be formed in any suitable manner. In one embodiment, as illustrated in FIG. 7, a plurality of tubes 190 (e.g., lead tubes) are glued together as illustrated at (a). Thereafter, the tubes 190 are filled, for example, with a molten wax at (b). The tubes 190 are then cut at (c) to form a curved face 192 at (c) (e.g., a curved face along one side of the body portion). For example, the tubes 190 may be cut to size or shape with a wire saw or other cutting device. The cutting may be performed to form tubes 190 have different lengths as described in more detail herein. Thereafter the wax is removed at (d) such that the tubes 190 now form different length bores for a collimator 194. Optionally the collimator is attached to a pixelated detector in a registered fashion such that at least some septa between bores are positioned over boundaries between pixels.

Figure 8:
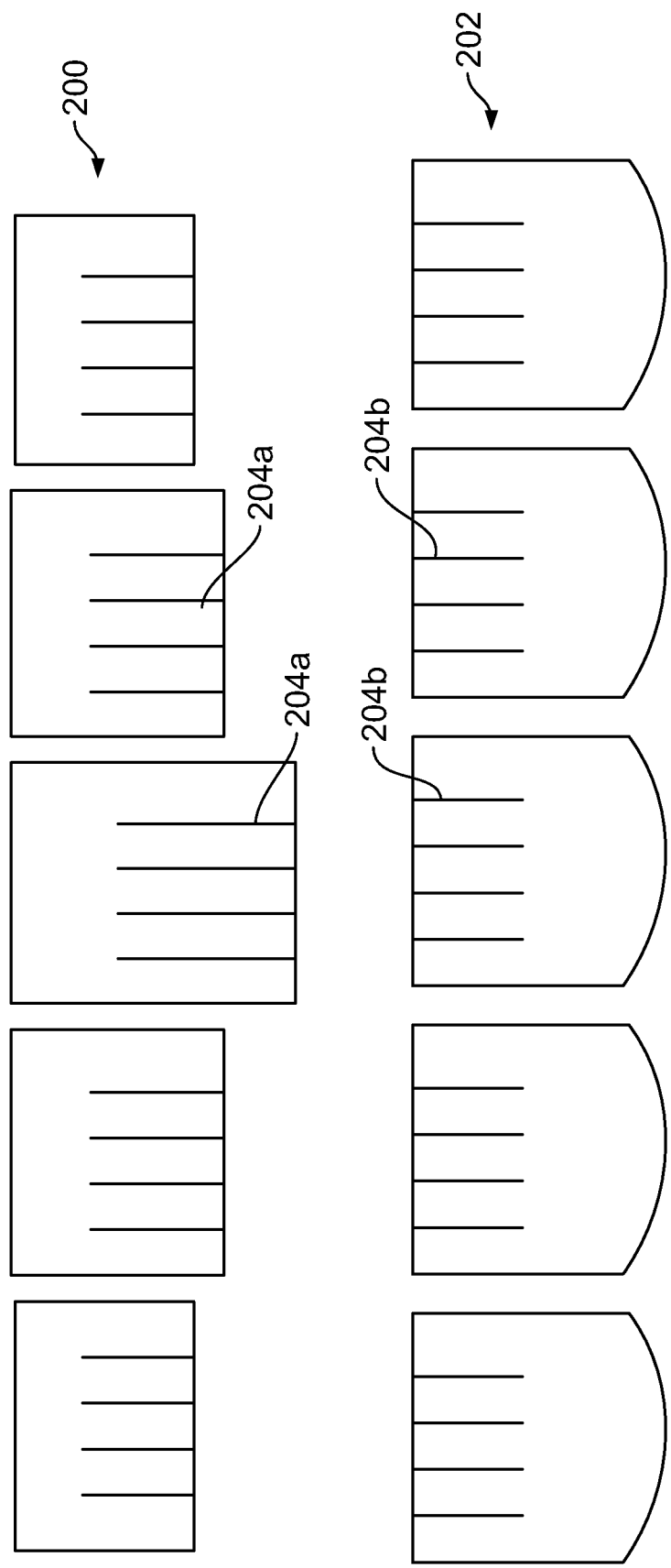
FIG. 8 is a diagram illustrating interlocking sheets for the manufacture of a collimator in accordance with an embodiment.

The manufacturing process may include using a plurality of interlocking sheets, such as the set of sheets 200 or 202 as shown in FIG. 8. For example, the sheets may be sized (e.g., length) and shaped to define a variable bore length collimator as described herein. The set of sheets 200 or 202 may correspond to different sections or portions of the collimator, such that complementary cuts 204*a* and 204*b* are formed to allow interlocking of the sheets 200 or 202 (top and bottom sheets as viewed in FIG. 7).

Figure 9:
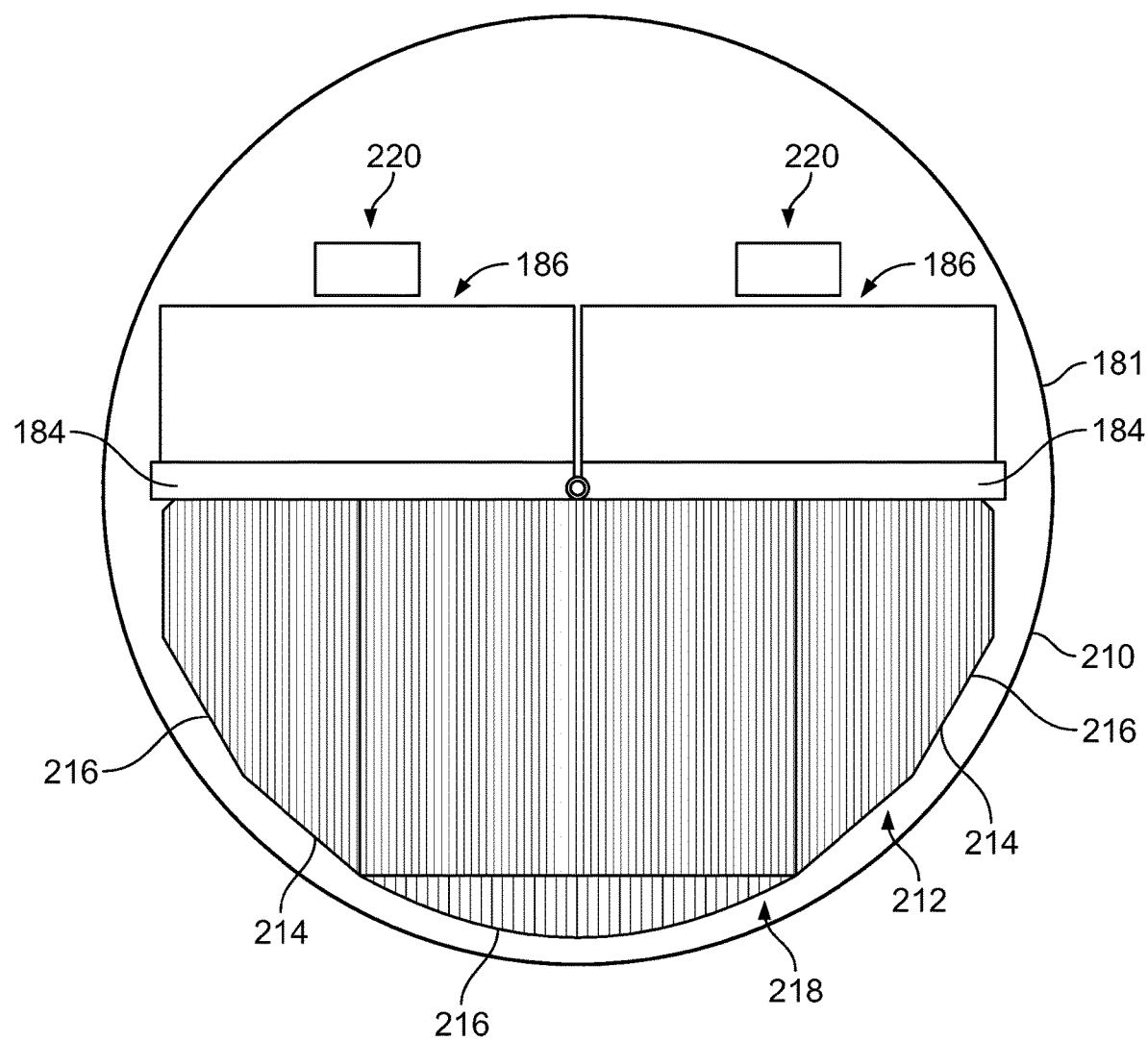
FIG. 9 is a diagram illustrating a collimator arrangement in accordance with another embodiment.

In some embodiments, two modules may be provided per detector head as shown in FIG. 9. However, it should be appreciated that additional modules may be provided (and the two modules shown are for illustration). In particular, within a single housing 210, two sets of CZT material 184 and corresponding electronics 186 may be provided. In this embodiment, a collimator 212 is similarly provided with collimator bores 214 having different lengths. As can be seen, in this embodiment, different sections 216 may be provided that having different curvatures, which may be determined based on the type and amount of movement to be provided within the housing 210. Again, as should be appreciated, the sections 216 are merely shown for ease of description and are not necessarily separate pieces joined together, but may be a single piece. Thus, in this embodiment, the collimator 212 has a curved face 218 that extends across two modules 220 defined by the two sets of CZT material 184 and corresponding electronics 186. It should be appreciated that additional modules 220 may be encompassed by the collimator 212 as desired or needed.

It should be noted that each detector unit may comprise an array of modules, for example 2×2, 2×3, 2×4 modules, etc. Generally, the pixel size of a pixelated NM detector may be selected to be about 1.5 mm to 3 mm, which may be due to physical constrains. In some embodiments, wherein the collimator is a registered collimator, the width of the collimator bore is the pixel to pixel separation minus the septa's thickness. The optimal length of the longest and shortest collimator bore may then be selected by knowing the desired minimum and maximum resolution and the tradeoff between the resolution and sensitivity at the working distance from the organ of interest. To be able to pivot without collision with the cover (or the nearby detector) the entire moving part of the detector, including the sensor, the collimator, electronics and optional shielding fit within a circular cross-section region 181 (e.g., cylindrical shielding or cover) centered about the picturing point (such as shown, for example, in FIGS. 6, 9, 10, and 11). When using a wider detector, for example made of two or three side by side modules, a larger aspect ration collimator (the ratio between the lengths of the longest and shortest collimator tubes) may be created, while efficiently filling the limiting circle.

It should be noted that different configurations of collimators may be provided. For example, in some embodiments, a collimator with a double pitch compared to the detector pitch may be provided (e.g., the pitch of collimator being twice the pitch of the detector). However, other different relative pitches may be provided. Using a collimator with a double pitch compared to the detector pitch allows for reducing the length of the collimator by half and reducing respectively the diameter of the detector unit. Thus, for example, the smaller detector unit allows the detector unit to be positioned closer to the subject before collision or colliding with adjacent detectors.

Figure 10:
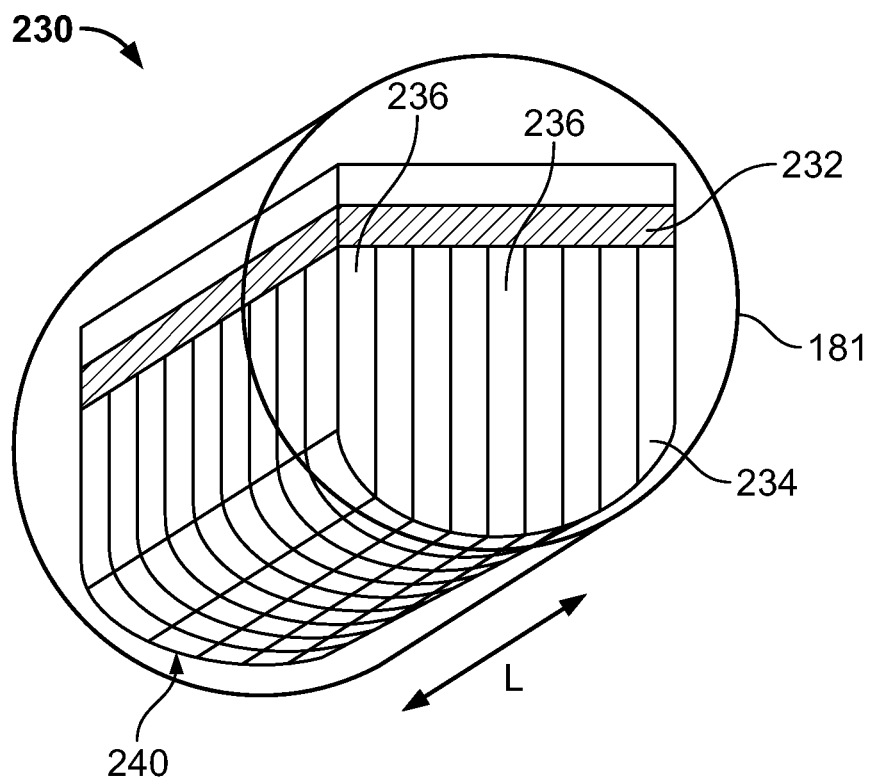
FIGS. 10 and 11 are diagrams illustrating a collimator arrangement in accordance with another embodiment.
Figure 11:
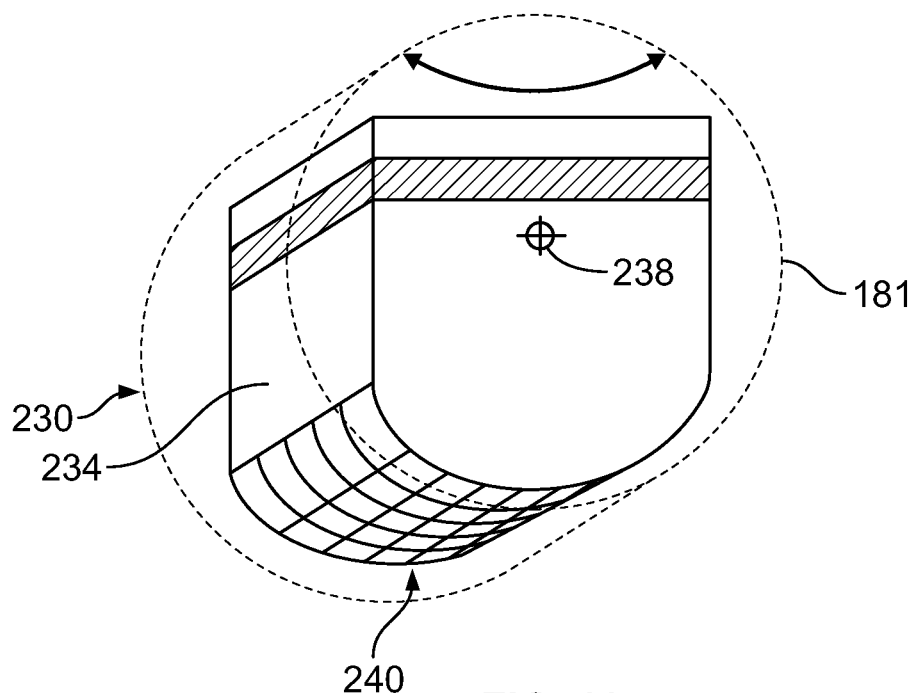

Different configuration of collimators also may be provided, such as curved in two-dimensions or three-dimensions. For example, as shown in FIGS. 10 and 11, which are isometric illustrations of FIGS. 6 and 9, a collimator 234 (which may be embodied as the collimator 172) may be provided that has varied bore length transverse to a longitudinal axis L of the detector 230. In this embodiment, the collimator bores 236 from front to back as viewed in FIGS. 9 and 10 have the same bore length, but the bore length is varied from side to side. An axis 238 of rotation may be provided as illustrated in FIG. 10 such that the curved face 240 rotates or swings about or parallel to the axis 238. However, in other embodiments, the axis 238 may be changed such that the curved face 240 may rotate transverse to the axis 238, such as if the axis 238 is positioned from one side to an opposite side of the detector 230 instead of from front to back as shown.

In some embodiments, a collimator 250 with a face 252 that curves from a center 254 in two-dimensions as shown in FIG. 12. For example, the curved face 252 is semi-spherical in this embodiment to allow swinging, for example, in two different directions (e.g., two orthogonal directions as illustrated by the arrows). This embodiment may be used, for example, for a detector pivoting in two directions.

Figure 13:
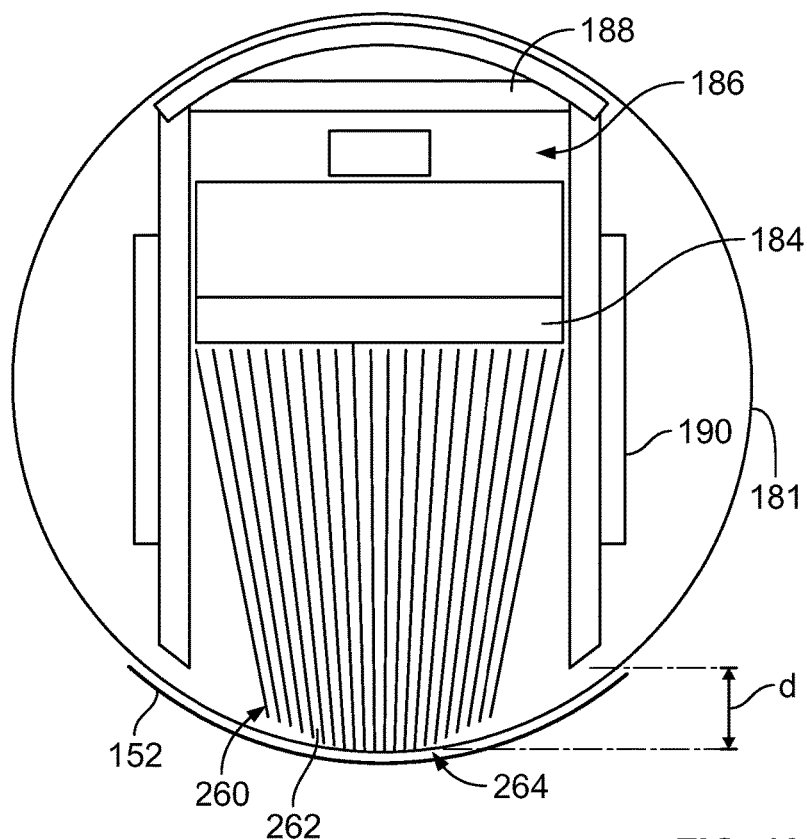
FIG. 13 is a diagram illustrating a collimator arrangement in accordance with another embodiment.
Figure 14:
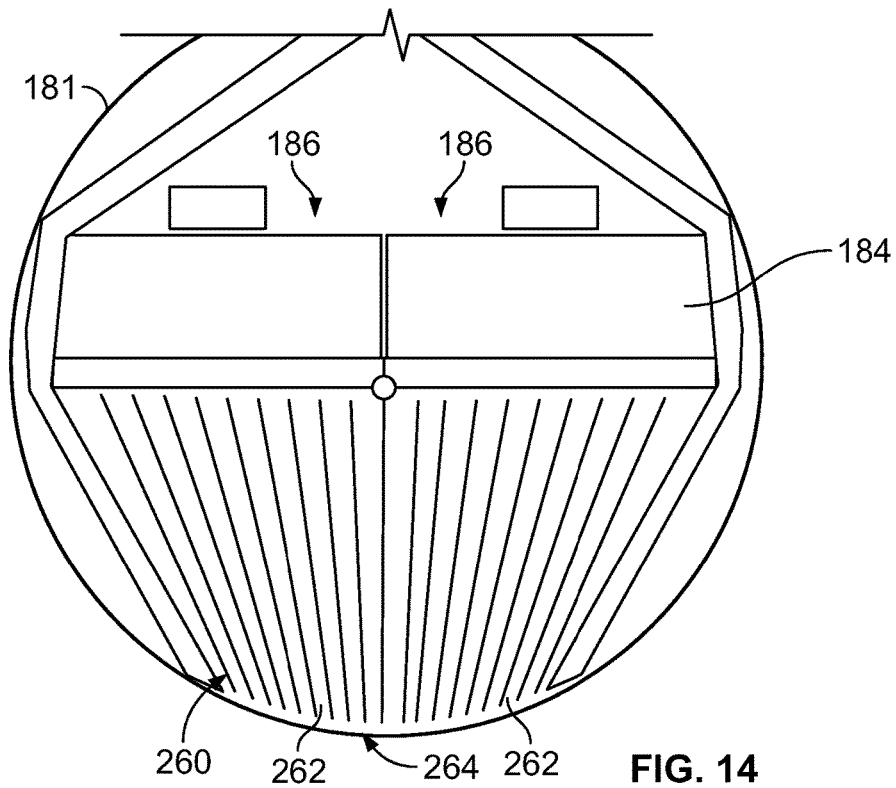
FIG. 14 is a diagram illustrating a collimator arrangement in accordance with another embodiment.

Other variations are contemplated. For example, as shown in FIGS. 13 and 14, a collimator 260 may be provided with variable length bores 262. However, in these embodiments, unlike the embodiments shown in FIGS. 5 and 8, respectively (where like numerals represent like parts), a fan-beam type collimation arrangement is provided instead of a parallel-hole arrangement. As can be seen, the bores 262 in this embodiment are angled towards a center region of the detector. Again, as should be appreciated, the bores 262 have different lengths to form a curved face 264. It should be noted that the fan beam configuration further reduces the distance from the face of the collimator to the patient at least for some portion of the face of the collimator and some pivot positions while efficiently remain within the circle 181 (e.g., limiting circle). This increase in resolution may contribute to better image quality. Additionally, as can be seen in FIG. 14, for a wide detector, the length of the tubes one the edges of the detector is similar to the length of the tubes in the center. Thus this configuration may provide a more even resolution across the detector, while at the same time reducing the distance to the patient.

Thus, various embodiments provide different motions of detector units, as well as different arrangements of collimators to allow the detector units to be positioned closer together and closer to the object to be scanned than conventional systems.

Figure 15:
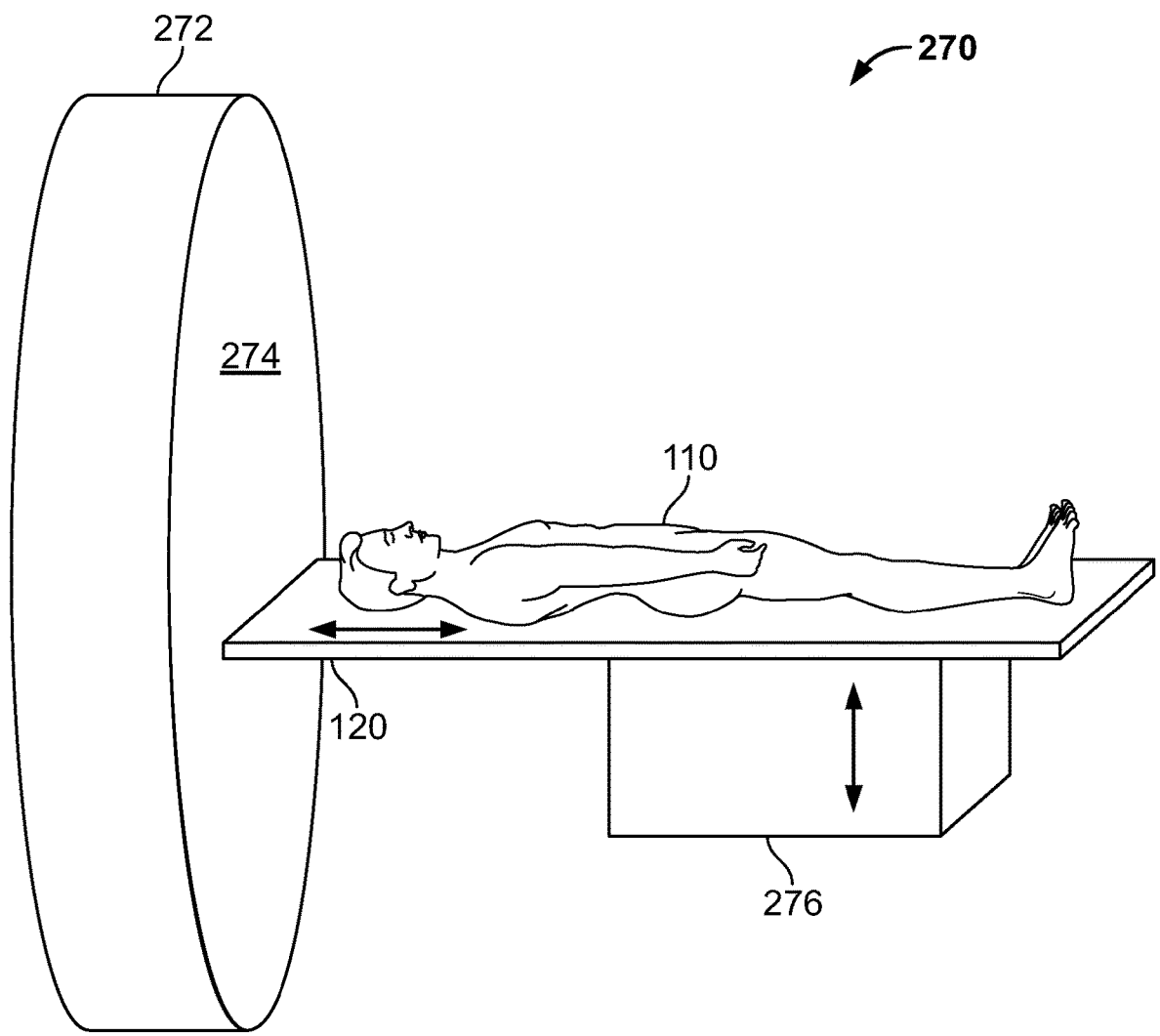
FIG. 15 is a diagram illustrating an imaging system in accordance with an embodiment in which one or more configurations of detectors may be implemented.

It should be noted that various embodiments may be implemented in different system configurations. For example, as shown in FIG. 15, an imaging system 270 may be provided that includes a gantry 272 with a bore therethrough. The gantry 272 may have coupled thereto different imaging detectors, for example, the imaging detectors 102 (as shown in FIG. 1). In this embodiment, the subject 110 is positioned on a patient table 120 that includes a support 276 (e.g., a patient table or bed mechanism) that allows movement of the patient table 120 as described herein. For example, the subject 110 may be moved upwards/downwards or left/right (along the examination axis) as viewed in FIG. 15. Thus, the subject 110 may be moved through the bore 274 and imaged as described in more detail herein, using one or more of the detector and/or collimator configurations described herein. Accordingly, in this embodiment, the system moves the subject 110 along the examination axis.

Figure 16:
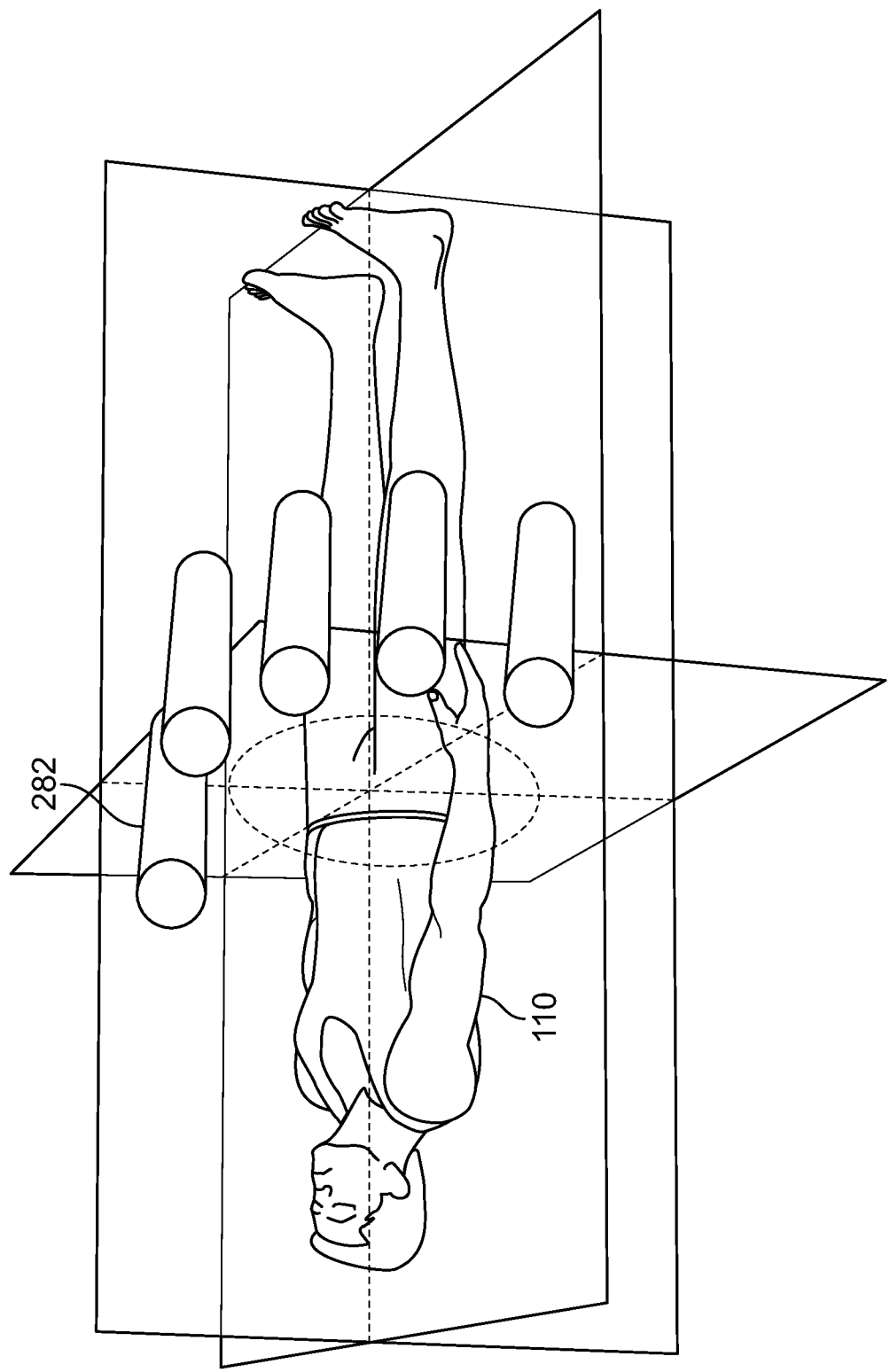
FIG. 16 is a diagram illustrates an imaging system in accordance with another embodiment in which one or more configurations of detectors may be implemented.

In another embodiment, for example, as shown in FIG. 16, and imaging system 280 may be provided wherein the imaging detectors 282 (which may be embodied as the imaging detectors 102 shown in FIG. 1) are positioned around at least a portion of the subject 110 (in some embodiments spaces partially or entirely around the subject 110). For simplicity and ease of description, only the detectors 282 and subject 110 are shown. However, one or more of the other system components as described herein are provided. The detectors 282 may be controlled or operated in this embodiment as described in more detail herein.

Thus, various embodiments may provide different configurations for positioning the detectors and/or subject 110 with respect to each other. The movement of the detectors may be, for example, radially or rotatably. In one embodiment, as shown in the imaging system 190 of FIGS. 17 and 18, a plurality of detectors 292 (e.g., the imaging detectors 102 shown in FIG. 1), are positioned and spaced evenly, such as distributed along a gantry evenly along the circumference of the gantry. For example, the detectors 292 are shown as spaced apart by 15 degrees, but other spacings may be provided. However, an uneven spacing and/or additional or fewer detectors 102 may be provided. As can be seen, the detectors 292 are movable radially inward and outward to position the detectors 292 adjacent to the subject 110 for imaging (shown in FIG. 18 in an imaging position or state). Thus, in this embodiment, the detectors 292 are shown in an outermost position in FIG. 17 and in an imaging position in FIG. 18. As should be appreciated, the detectors 292 are movable different distances (e.g., one or more detectors 292 moved different distances) depending on the size, shape, etc., of the subject 110.

Figure 17:
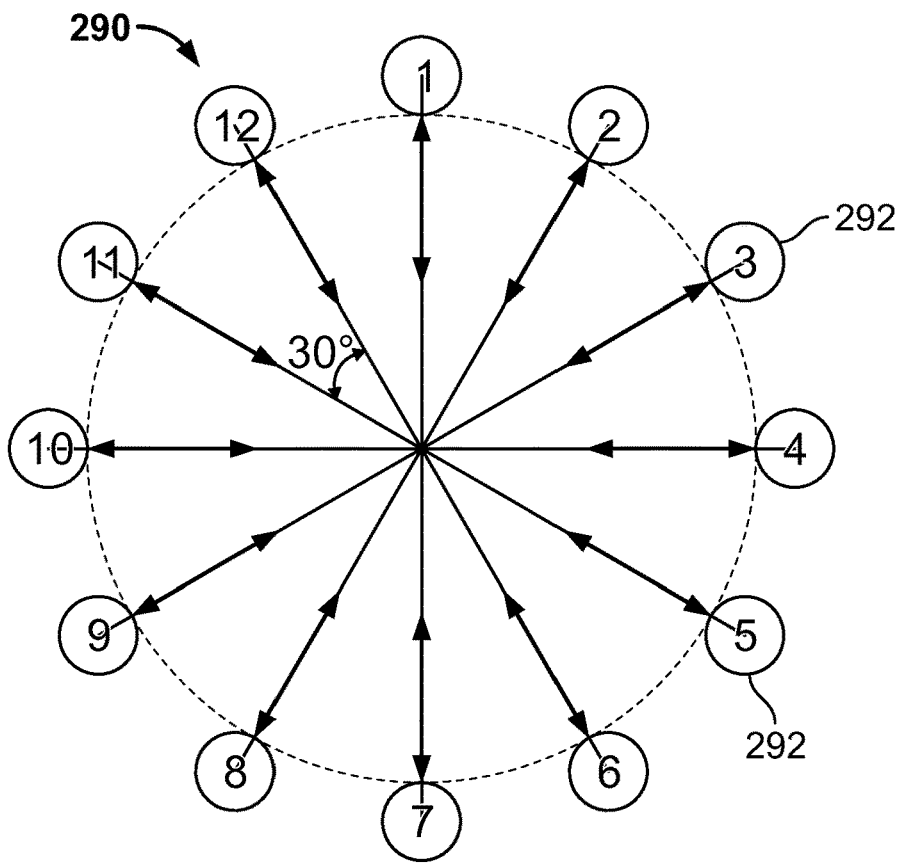
FIGS. 17 and 18 are diagrams illustrating motion of detectors in accordance with an embodiment.
Figure 18:
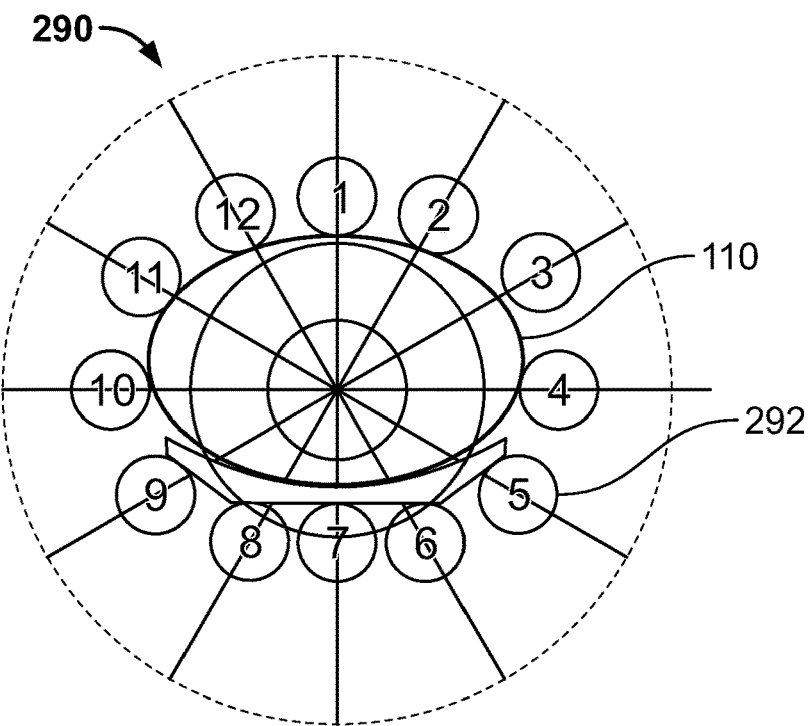
Figure 19:
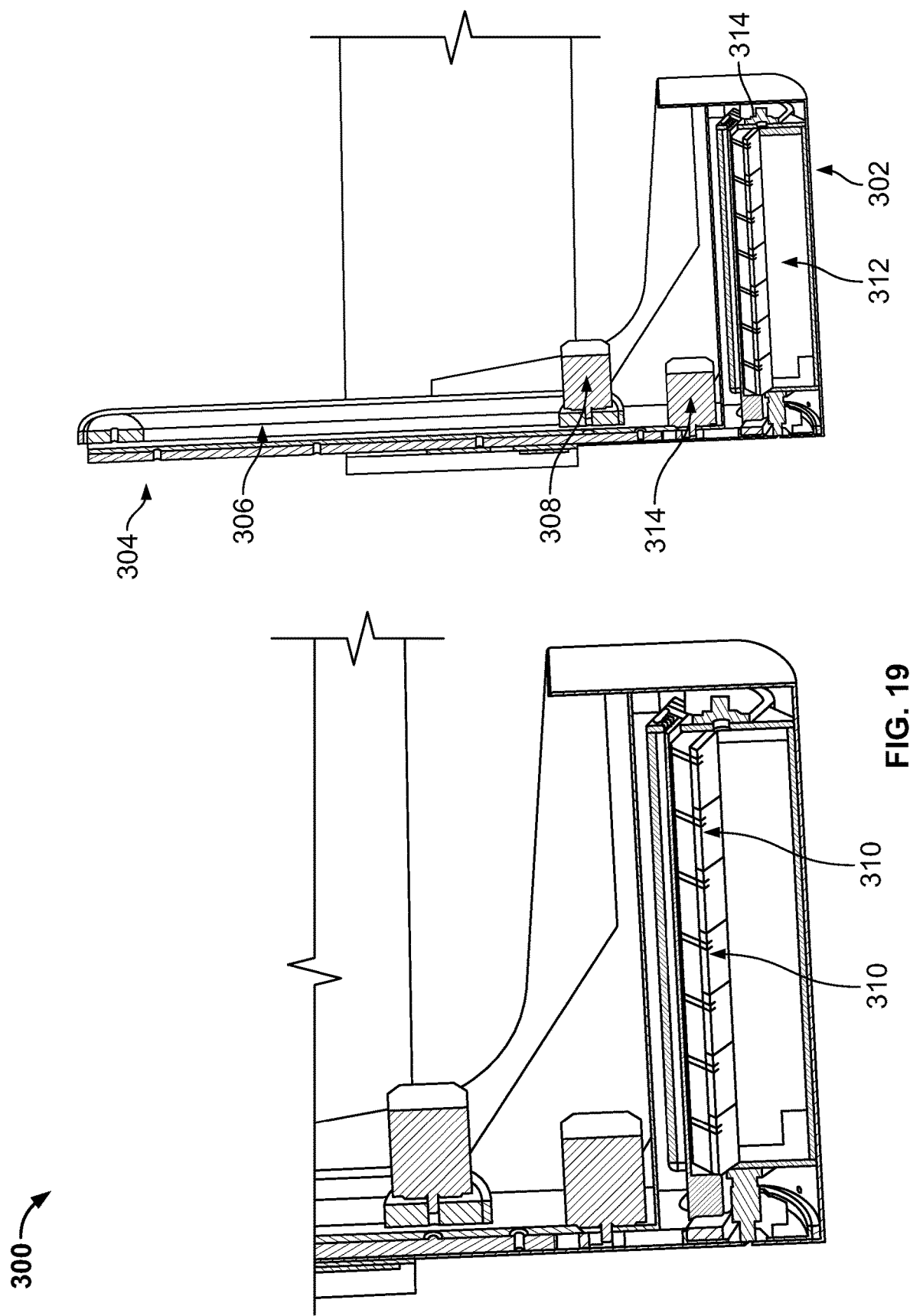
FIG. 19 is a diagram illustrating a detector arm configuration in accordance with an embodiment.

The mechanism or components to moving the imaging detectors in various embodiments may be provided using different arrangements. One arrangement 300 is shown in FIG. 19 illustrating an imaging detector configuration wherein a detector head 302 is mounted at one end of an arm 304 that includes a rail 306 to allow radial movement, such as shown in FIGS. 17 and 18. The movement may be controlled using a radial motion motor 308. The detector head 302 in this embodiment includes a plurality of imaging modules 310 (illustrated as CZT modules) that may be aligned in one or more rows (a single row is illustrated in the embodiment shown). As can be seen, a collimator 312 may be provided and coupled to one or more of the imaging modules 310. The collimator 312 may be provided as described herein. Additionally, the imaging modules 310 are coupled to a support 314 (e.g., a rod) that allows rotation or pivoting movement of the imaging modules 310 within the detector head 302. For example, a motor, such as a sweep motor 314 may be provided to control and move the imaging modules 310 to sweep across a region of interest (e.g., rotate or pivot a defined number of degrees).

Additionally, different configurations may be provided. For example, within a single cover or a single detector head, multiple detector units or modules may be provided. Additionally, one or more detectors may be fixed or mounted (or within) the patient table 120 or a support portion thereof.

Figure 20:
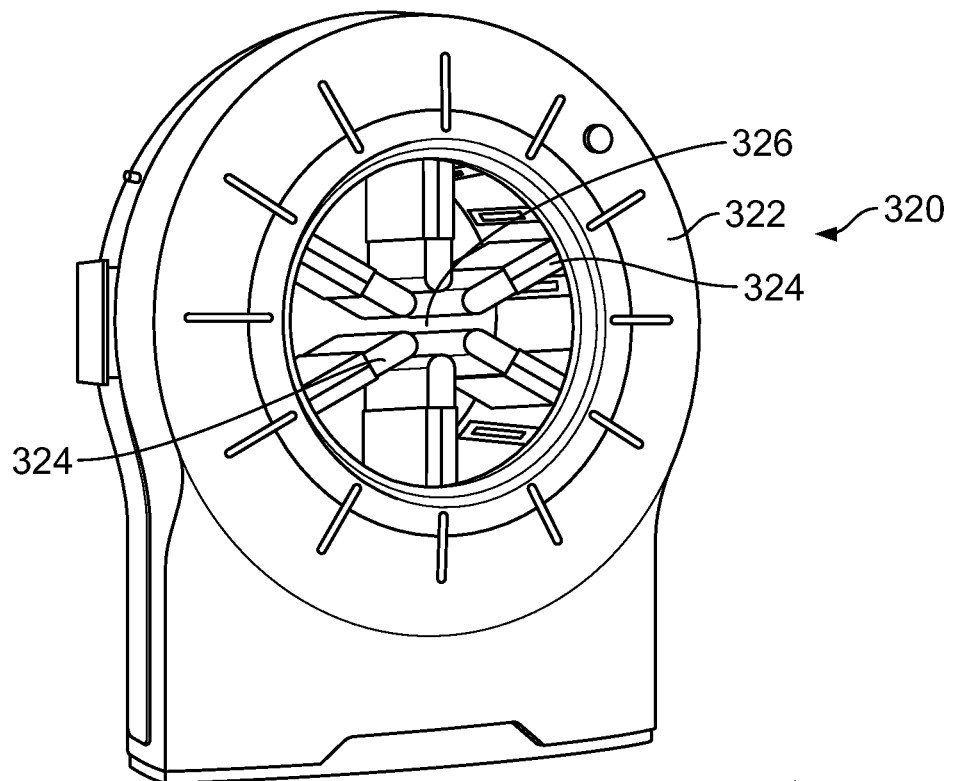
FIG. 20 is a perspective view of an imaging system in accordance with another embodiment.
Figure 21:
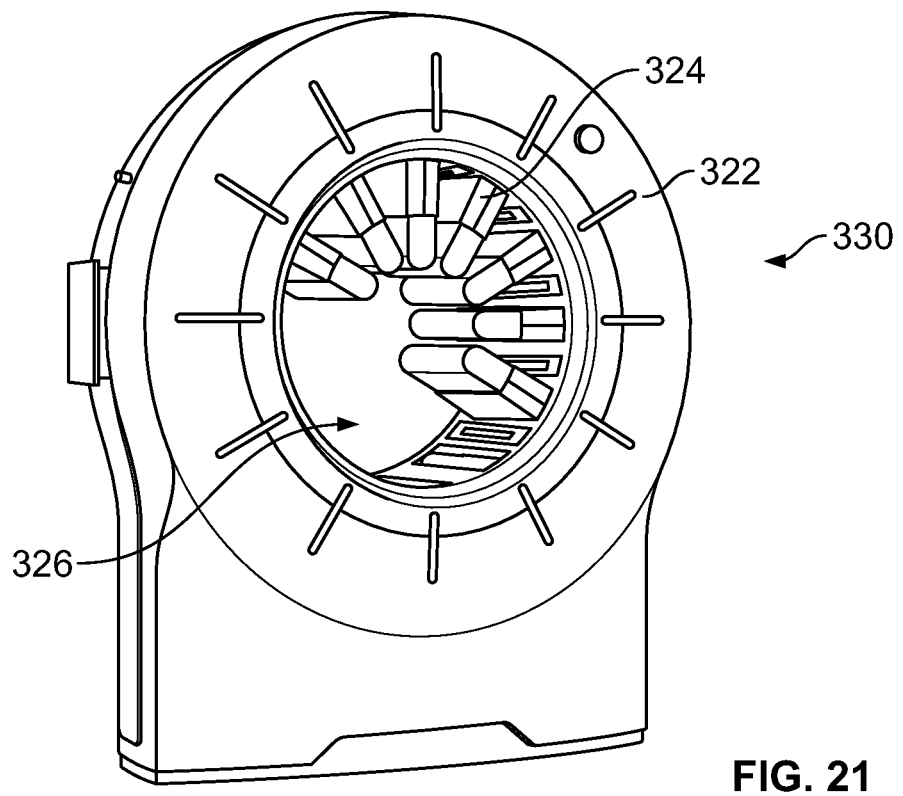
FIG. 21 is a perspective view of an imaging system in accordance with another embodiment.

It should be noted that a plurality of arms supporting the detector units may be provided in different configurations. For example, as shown in FIG. 20, a system 320 may be provided with a gantry 322 having a plurality of arms 324 (e.g., movable supports as described herein) that extend and/or are movable radially inward and outward from the gantry 292. It should be noted that the arms 324 are spaced apart circumferentially around the entire bore 326 in this embodiment. It also should be noted that additional or fewer arms and different spacing between arms 324 may be provided. The arms 324 may be movable as described herein and may be embodied as the detector carriers 116 (shown in FIG. 1) in some embodiments. Additionally, each arm 294 may support one or more detector units or modules (e.g., the detector units 114 shown in FIG. 1). Other variations include arms 324 that are provided along only a portion of the circumference of the bore 326 as illustrated in the system 330 of FIG. 21. It should be noted that although the arms 324 are illustrated along about 180 degrees, the arms 294 may be provided along more or less of the bore 326, such as more or less than 180 degrees. It should be noted that for the configuration shown in FIG. 21, rotations greater than 180 degrees may be used to provide imaging in both prone and supine positions of the subject 110. For example, in some embodiments, rotation of about 210 degrees is provided. However, the rotation may be more or less than 210 degrees as desired or needed.

Additionally, different configurations may be provided. For example, a linear type of design may be provided, such as described and shown in FIG. 11 in co-pending U.S. patent application Ser. No. 14/016,943, entitled "Methods and Apparatus for Imaging with Detectors having Moving Detector Heads", which is hereby incorporated by reference in its entirety.

Figure 22:
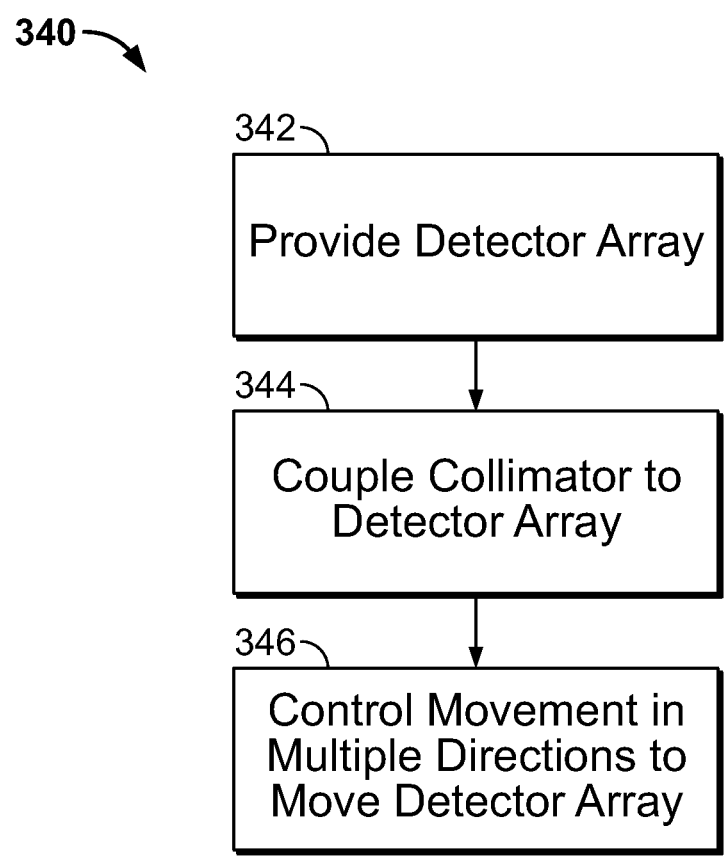
FIG. 22 is a flowchart of a method in accordance with various embodiments.

Various embodiments also provide a method 340 as shown in FIG. 22. The method 270 includes providing a detector array at 342, for example, a CZT array with associated electronics as described herein. A collimator is coupled to the detector array at 344. For example, a collimator with different length bores and/or a curved face as described herein may be used. However, in other embodiments, a planar face collimator may be used. The method 340 additionally includes controlling movement in multiple directions to move the detector array at 346. For example, as described herein, the detector array may be translated and rotated or swung concurrently.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. An imaging system comprising:
  a gantry including first and second support members;
  a plurality of detector units mounted to the gantry, the plurality of detector units individually movable including translational movement and rotational movement, wherein the plurality of detector units include a first group of detector units in a first array mounted to a first support member and a second group of detector units in a second array mounted to a second support member, wherein the first array and second array are disposed on opposite sides of a subject to be imaged, wherein the first detector units are configured to move parallel to each other and with the first support member along a translational direction parallel to the first and second support members for the translational movement, and wherein the second detector units are configured to move parallel to each other and with the second support member along the translation direction for the translational movement; and a controller configured to control movement of the plurality of detector units to acquire Single Photon Emission Computed Tomography (SPECT) data, the movement including both the translational movement and the rotational movement coordinated to position the plurality of detector units adjacent to the subject.

2. The imaging system of claim 1, wherein the controller is configured to control one or more of the plurality of detector units to concurrently perform the translational movement and the rotational movement.

3. The imaging system of claim 1, further comprising a housing for each of the plurality of detector units, wherein the plurality of detector units are movable within respective housings.

4. The imaging system of claim 3, wherein the rotational movement comprises rotating motion relative to the housing and within the housing.

5. The imaging system of claim 1, further comprising at least one collimator coupled to a corresponding one of the plurality of detector units and disposed within a housing of the corresponding one of the plurality of detector units, the collimator having collimator bores of different lengths to form a non-planar face, wherein the non-planar face has a shape corresponding to an interior of the housing of the corresponding one of the plurality of detector units.

6. The imaging system of claim 5, wherein the different lengths of collimator bores define a higher resolution region in a middle section of the collimator.

7. The imaging system of claim 5, further comprising a plurality of cadmium zinc telluride (CZT) pixilated detector modules within at least one of the plurality of detector units, the plurality of modules coupled to a single collimator.

8. The imaging system of claim 5, wherein the non-planar face extends along one axis.

9. The imaging system of claim 5, wherein the non-planar face is non-planar in three-dimensions to form a semi-spherical shape.

10. The imaging system of claim 5, wherein the collimator bores are aligned to form a parallel hole type collimation wherein the collimator bores are aligned in parallel.

11. The imaging system of claim 5, wherein the collimator bores are aligned to form a fan-beam type collimation.

12. The imaging system of 1, further comprising an imaging unit forming part of the imaging system and configured to acquire image information different than the SPECT data, the controller configured to control movement of the plurality of detector units to focus at least one of the plurality of detector units on a region of interest, wherein the movement is controllable by at least one of manual positioning, automatically using image information from different imaging modality separate from the imaging system, or automatically using image information from the imaging unit.

13. The imaging system of 1, wherein the plurality of detector units are configured to acquire Single Photon Emission Computed Tomography (SPECT) data, and further comprising an x-ray Computed Tomography (CT) imaging unit forming part of a combined SPECT/CT imaging system and configured to acquired CT image information, the controller configured to control movement of the plurality of detector units to focus at least one of the plurality of detector units on a region of interest, wherein the movement is controllable automatically using the CT image information acquired by the CT imaging unit.

14. The imaging system of 1, wherein the plurality of detector units are configured to acquire Single Photon Emission Computed Tomography (SPECT) data, and further comprising a stand-alone x-ray computed tomography (CT) imaging unit configured to acquired CT image information, the controller configured to control movement of the plurality of detector units to focus at least one of the plurality of detector units on a region of interest, wherein the movement is controllable automatically using the CT image information acquired by the stand-alone x-ray CT imaging unit.

15. The imaging system of 1, further comprising a collimator is coupled to at least one of the plurality of detector units, the collimator having twice the pitch compared to a pitch of the detector unit to which the collimator is coupled.

* * * * *